United States Patent [19]
Grandics et al.

[11] Patent Number: 5,773,224
[45] Date of Patent: Jun. 30, 1998

[54] IMMUNOSELECTION SYSTEM FOR CELL ELUTION

[76] Inventors: Peter Grandics; Susan Szathmary, both of P.O. Box 188158, Carlsbad, Calif. 92009

[21] Appl. No.: 598,560

[22] Filed: Feb. 12, 1996

[51] Int. Cl.$^6$ .................. G01N 33/53; G01N 33/567; G01N 33/543
[52] U.S. Cl. .................. 435/7.2; 435/7.1; 436/518
[58] Field of Search .................. 435/7.1, 7.2, 262, 435/183, 325; 436/518; 530/412, 413; 935/90, 92

[56] References Cited

U.S. PATENT DOCUMENTS

| | | | |
|---|---|---|---|
| 4,228,237 | 10/1980 | Hevey et al. | 435/7 |
| 4,298,685 | 11/1981 | Parikh et al. | 435/7 |
| 4,468,470 | 8/1984 | Aalberse | 436/539 |
| 5,518,882 | 5/1996 | Lund et al. | 435/6 |

FOREIGN PATENT DOCUMENTS

92/16841  10/1992  European Pat. Off. .

*Primary Examiner*—Lila Feisee
*Assistant Examiner*—Yvonne Eyler
*Attorney, Agent, or Firm*—Merchant, Gould, Smith, Edell, Welter & Schmidt

[57] ABSTRACT

The recovery of immunoselected cells is improved by using a specific affinity elution system utilizing members of an immobilized ligand/antiligand pair, with soluble ligand used for elution. In one embodiment, Immobilized heparin adsorbent is coated with biotinylated antithrombin III which is then crosslinked with avidin, thereby greatly increasing the binding affinity of antithrombin III for heparin. The resulting adsorbent effectively captures biotin-labeled target cells and allow facile elution of immunoselected cells with soluble heparin. The cell separation system is capable of both positive and negative selection.

15 Claims, 5 Drawing Sheets

IMMUNOSELECTION SYSTEM FOR CELL ELUTION

BACKGROUND OF THE INVENTION

This invention is directed to a method of cell separation employing immunoselection.

Cell separation is a rapidly growing area of biomedical and clinical research. The principle is to target certain cell surface markers with specific affinity ligands in order to achieve selective, reversible attachment of the target cell population to a solid phase. In a subsequent step, the nonspecifically adsorbed cells are removed by washing followed by the release of target cells. The specific affinity ligands may be antibodies, lectins, receptor ligands, or other ligands that bind proteins, hormones, carbohydrates, or other molecules with biological activity.

Cell separation techniques employing affinity typically employ immunotechniques such as immunoselection. Immunoselection encompasses techniques in which the specificity of selection is conferred by an antibody. This is exemplified by the affinity of an antibody for a specific cell surface antigen. Immunoselection may be positive or negative selection. Positive immunoselection allows the direct selection and recovery of a specific cell population from a heterogeneous group of cell types. It allows the selective enrichment and purification of targeted antigen-bearing cells. Positively selected cell populations are purer than those obtained by negative selection but stimulation of cells by antibody bound to cell surface receptors is a possibility which may affect the biological utility of cells selected by positive selection. This suggests that both positive and negative cell selection may play an important role in isolating clinically useful cell populations.

Negative selection involves the elimination of specific cell types from a heterogeneous population. Negative selection techniques have a limitation in that although specific component types can be removed, the remaining components do not provide a pure population. The advantage, however, is that negatively-selected cells remain typically unaffected by the selection procedure, i.e., target cells can escape activation or stimulation.

Potential clinical use of cell separation systems requires a sterile, closed apparatus in which large quantities of viable, specific cell populations can be obtained rapidly from crude cell suspensions or directly from blood. Several attempts have been made in the past to create such a system. The most convenient and scalable techniques followed the standard column chromatography format. These methods included the immobilization of antibodies directed against cell surface antigens to the chromatography particles. Immobilized lectins were also used to target cell surface glycoproteins. Since cells are much larger than the capture proteins (antibodies or lectins), multiple linkages are needed to achieve sufficient cell retention in the column. Incubation of the cell suspension in the column bed is also important for efficient cell retention.

The high affinity of avidin-biotin interaction has made cell separation in a dynamic fashion possible. Biotin-labeled antibody is used to mark cell surface antigens. The cell-antibody complex is then adsorbed to an avidin derivatized matrix. Several patents describe the use of avidin-biotin system in immunoselection (for reference please see U.S. Pat. Nos. 4,298,685, 4,228,237 and 4,468,470). Elution of the selected cells is typically carried out by mechanical shear (agitation or high flow rates), or proteolytic enzyme digestion.

Some other proposed methods include reduction of disulfides or cleavage of specific linkages by enzymatic or chemical agents inserted somewhere between the capture solid surface and the target cells. Such techniques may include protease digestion of marker antibodies or coupling peptides, oligosaccharides cleavable with glycolytic enzymes, or chemical bonds broken under mild conditions that will preserve biological activity, such as oxidizing, reducing, basic, or acidic conditions. Because of the extreme complexity of cell surfaces and the desire to maintain high cell viability and functional integrity during selection, it is very difficult to find an enzymatic or chemical elution method which has no effect on the cell structure and/or function. Mechanical agitation/elution can be damaging to the cell membrane and reduce cell viability.

It would be advantageous to provide an improved elution technique which would allow mild cell elution from the solid phase adsorbent. This technique should be affinity-based allowing specific, high affinity binding of cells to the solid phase as well as rapid, mild elution with a competing ligand. The technique should eventually allow direct cell isolation from whole blood in a dynamic fashion without interference of blood constituents or therapeutic anticoagulants. The isolated cells may find use in bone marrow/organ transplantation, gene therapy, and the treatment of a variety of malignancies.

SUMMARY OF THE INVENTION

Pursuant to the invention, a novel immunoselection system is developed employing a ligand-antiligand pair to achieve elution of specifically-bound cells from the solid phase adsorbent under mild, physiological conditions. In an illustrative embodiment, a surface specific antibody (e.g., mouse monoclonal antibody) is used to bind to a specific cell population. Unbound antibody is then washed away and the cell suspension is incubated with an anti-mouse immunoglobulin-biotin conjugate to form a complex of biotin-antimouse/mouse antibody bound to the cell population. Excess biotin-antimouse antibody is then removed by washing. The labeled cell suspension is passed over a column of large bead adsorbent to which heparin is immobilized and to which a complex of biotin-human antithrombin III/avidin complex is adsorbed. The targeted cell population is bound via mouse antibody/antimouse-biotin/avidin/biotin-antithrombin III complexes to the heparin derivatized surface, using the capability of avidin to bind to more than one biotin molecule. Unadsorbed cells are removed by washing from the column. The bound cells are then eluted with heparin which competes with the immobilized heparin for the antithrombin III. This approach has particular advantages for removing and recovering certain cell populations from bone marrow, cord blood or isolating mixed populations of T cells or tumor cells. Similarly, peripheral blood cells or tissue cell suspensions, e.g., malignant cells from biopsies or normal cells from e.g., spleen can be enriched using this method. The recovered cells (e.g., hematopoietic stem cells) can be used in clinical applications.

In one embodiment of the invention, an immunoselection method for isolating a cell type from a heterogeneous cell suspension by affinity elution comprises the steps of:

(1) reacting the cell suspension with a first reagent having specific binding affinity for a surface molecule of a cell type in the heterogeneous suspension to form first reagent/cell type complexes in the cell suspension;

(2) reacting the first reagent-cell type complexes with a biotinylated second reagent having specific binding affinity for the first reagent to form biotinylated second reagent/first reagent/cell type complexes in the cell suspension;

(3) providing a solid capture surface onto which an immobilized ligand is covalently linked, the ligand being a member of a ligand-antiligand pair and capable of existing in soluble form;

(4) noncovalently adsorbing to the solid capture surface a biotinylated antiligand;

(5) reacting the cell suspension containing the biotinylated second reagent/first reagent/cell type complexes with the solid capture surface to which the biotinylated antiligand is adsorbed and with avidin to bind the biotinylated second reagent/first reagent/cell type complexes to the biotinylated antiligand through an avidin bridge to bind the cell type to the solid capture surface; and (6) eluting the cell type from the solid capture surface by dissociating the ligand-antiligand binding pair with soluble ligand, thus producing eluted cells of the cell type.

The cell type can be a target cell type, in which case the immunoselection method is a positive immunoselection method. The target cell type can be a cell type selected from the group consisting of hematopoietic stem cells, tumor cells, fetal cells from the peripheral blood of pregnant women, lymphocytes, and virus-infected cells. Alternatively, the cell type can be an undesired cell type, in which case the immunoselection method is a negative immunoselection method.

Typically, the affinity of the ligand-antiligand complex is such that the ligand-antiligand complex has a dissociation constant ($K_d$) of about $10^{-8}$ M.

Typically, the ligand-antiligand pair is heparin-antithrombin III.

Typically, the first reagent is a monoclonal antibody specific for a cell surface antigen and the second reagent is a biotinylated antibody specific for the first antibody.

The heterogeneous cell suspension can be derived from a source selected from the group consisting of bone marrow, peripheral blood, and cord blood.

Alternatively, instead of separate first and second reagents, a first reagent that is covalently bound to biotin or can be noncovalently associated with biotin can be used and the second reagent can be eliminated. In general, this embodiment of the invention comprises:

(1) reacting the cell suspension with a first reagent covalently linked to biotin or noncovalently linkable with biotin and having specific binding affinity for a surface molecule of a cell type in the heterogeneous suspension to form biotinylated first reagent/cell type complexes in the cell suspension;

(2) providing a solid capture surface onto which an immobilized ligand is covalently linked, the ligand being a member of a ligand-antiligand pair and capable of existing in soluble form;

(3) noncovalently adsorbing to the solid capture surface a biotinylated antiligand;

(4) reacting the cell suspension containing the biotinylated first reagent/cell type complexes with the solid capture surface to which the biotinylated antiligand conjugated to avidin is adsorbed and with avidin to bind the biotinylated second reagent/first reagent/cell type complexes to the biotinylated antiligand through an avidin bridge to bind the cell type to the solid capture surface; and (5) eluting the cell type from the solid capture surface by dissociating the ligand-antiligand binding pair with soluble ligand, thus producing eluted cells of the cell type.

BRIEF DESCRIPTION OF THE DRAWINGS

These and other features, aspects, and advantages of the present invention will become better understood with reference to the following description, appended claims, and accompanying drawings where:

DESCRIPTION

Pursuant to the invention, the selection of a desired cell subpopulation can be performed by both positive or negative selection methods.

Figure 1:
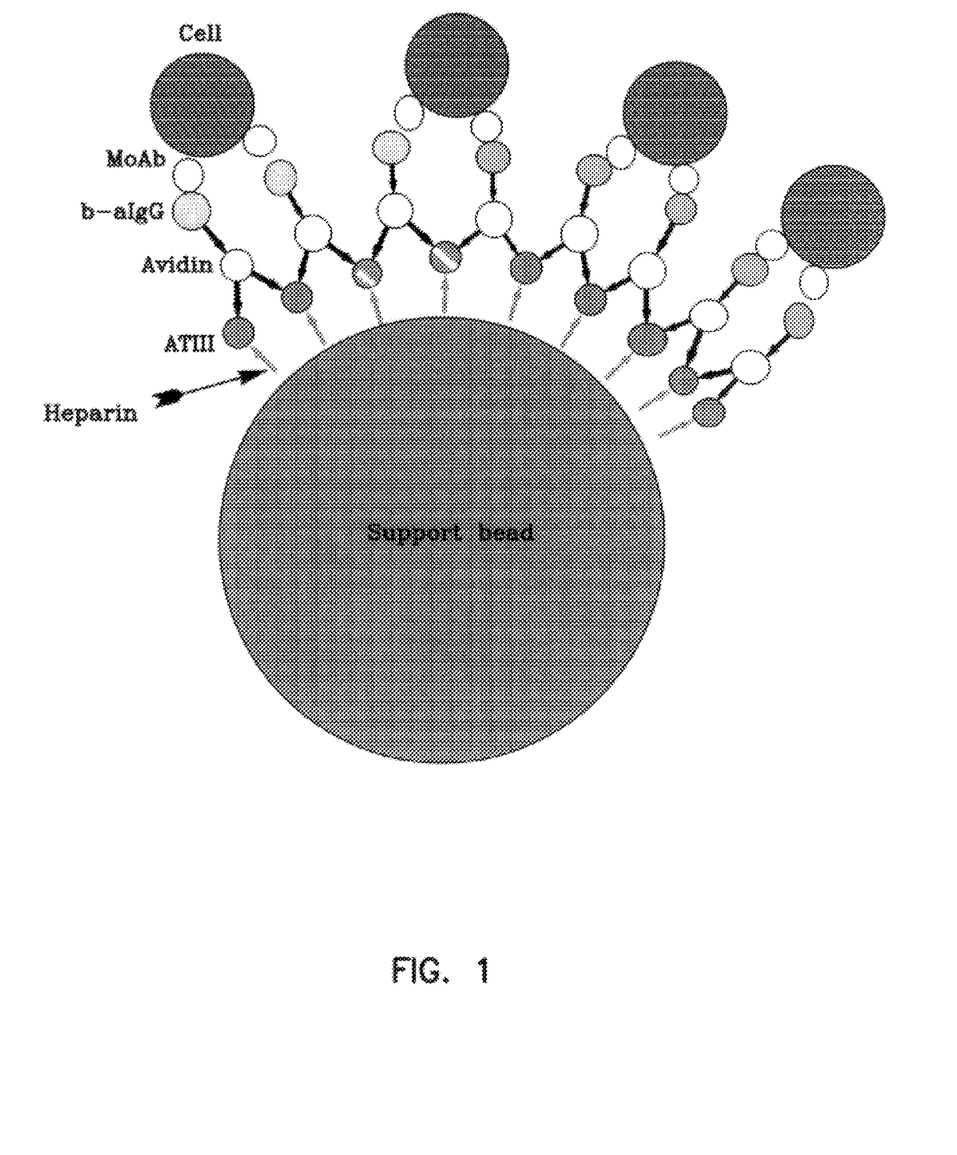
FIG. 1 is a schematic diagram of the cell selection system described in the preferred embodiments.
Figure 2A:
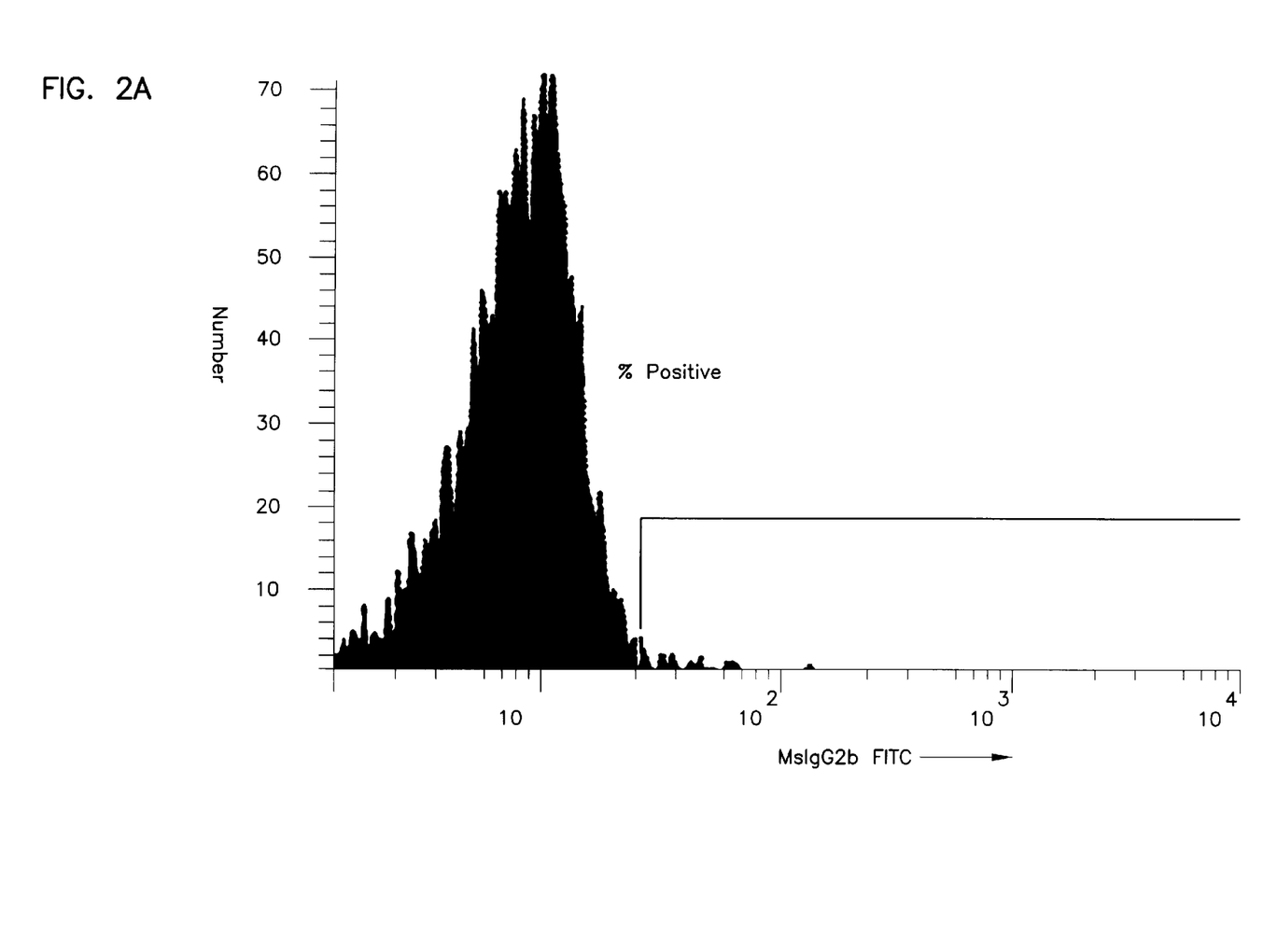
FIG. 2 is a fluorescence-activated cell sorter analysis demonstrating selective enrichment of $CD^{4+}$ T lymphocytes from a suspension of human white blood cells; A1 and B1 are controls; A2 is peripheral lymphocytes before selection; B2 is peripheral lymphocytes after selection using the method of the present invention.
Figure 2B:
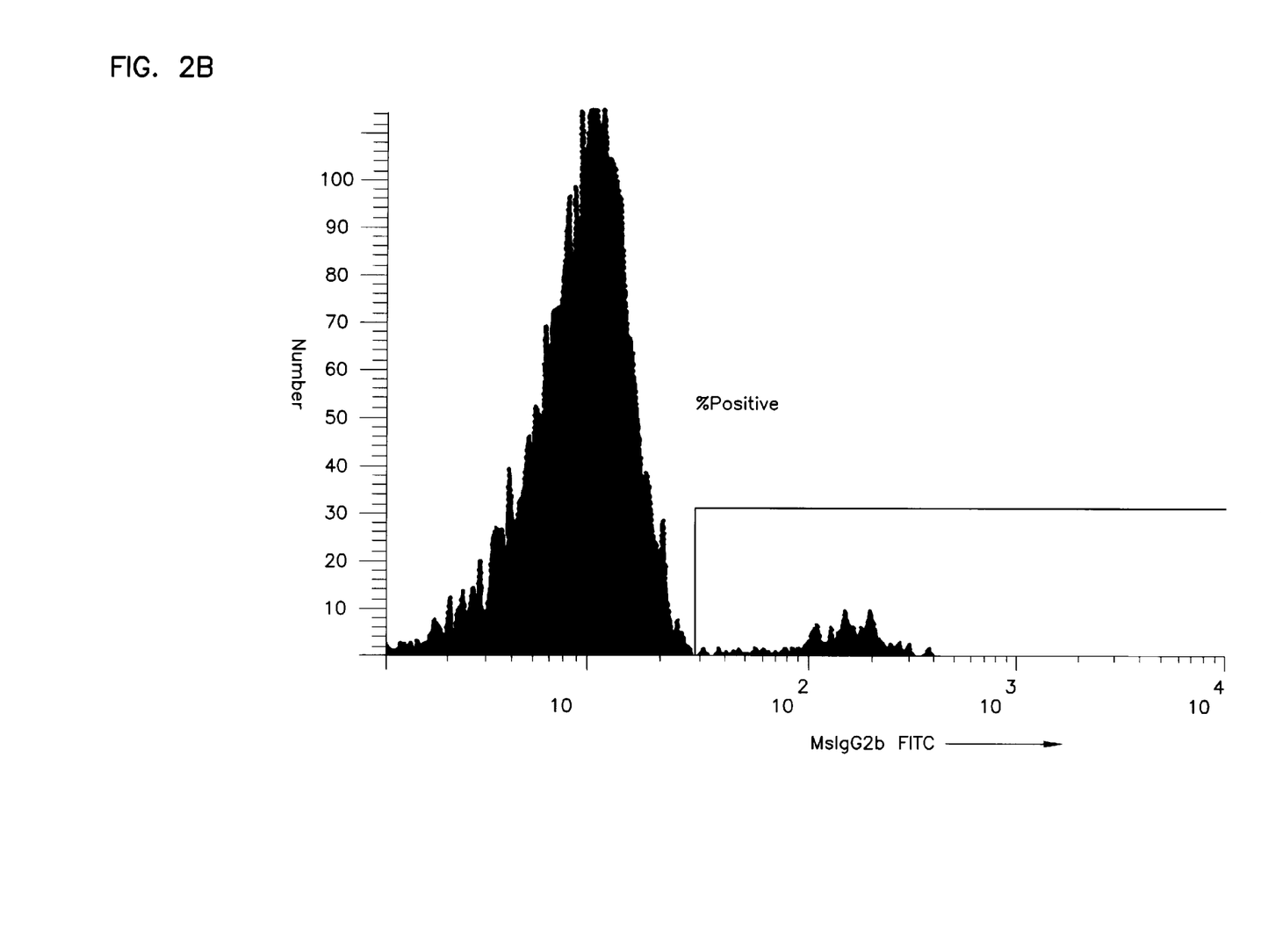
Figure 2C:
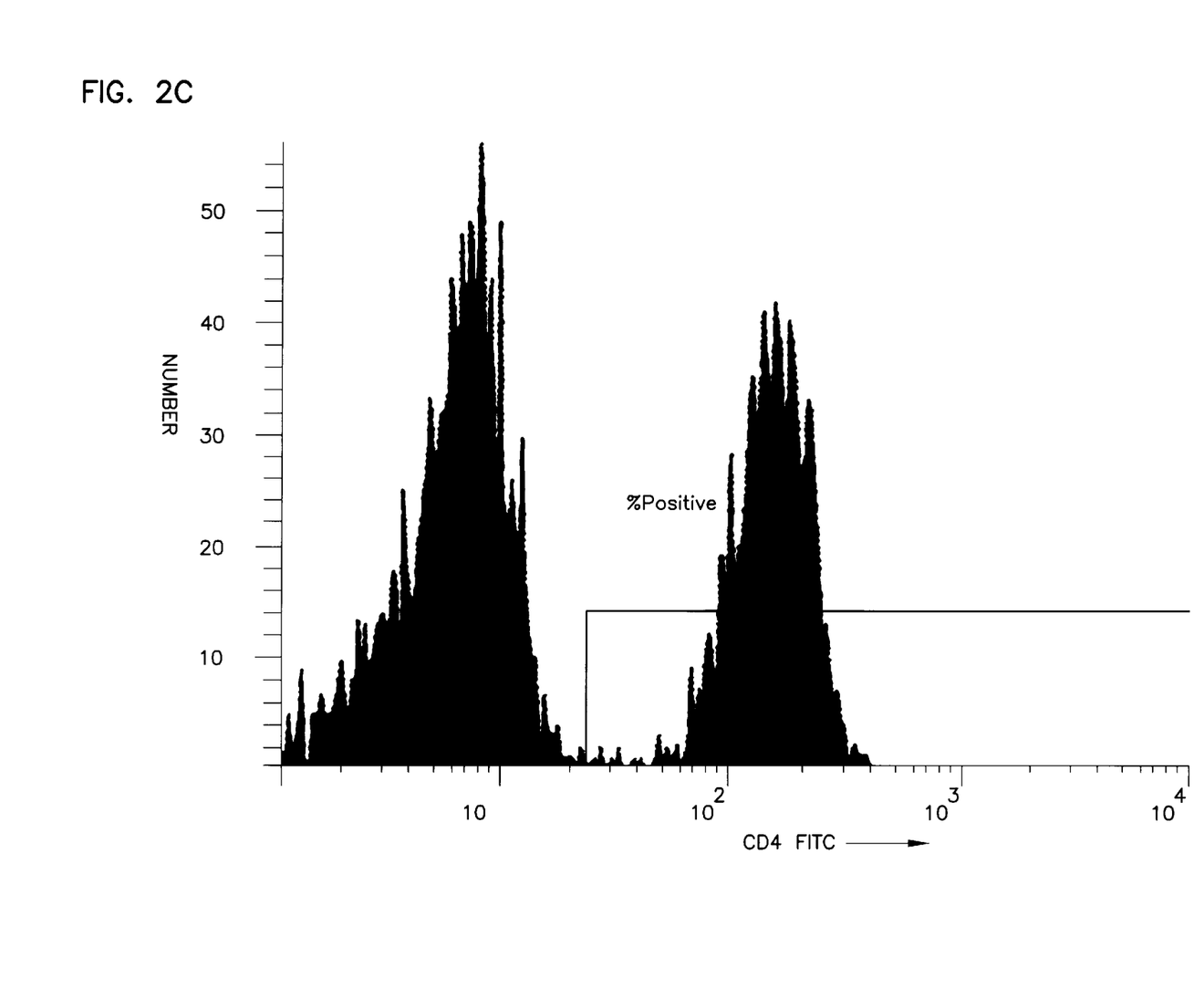
Figure 2D:
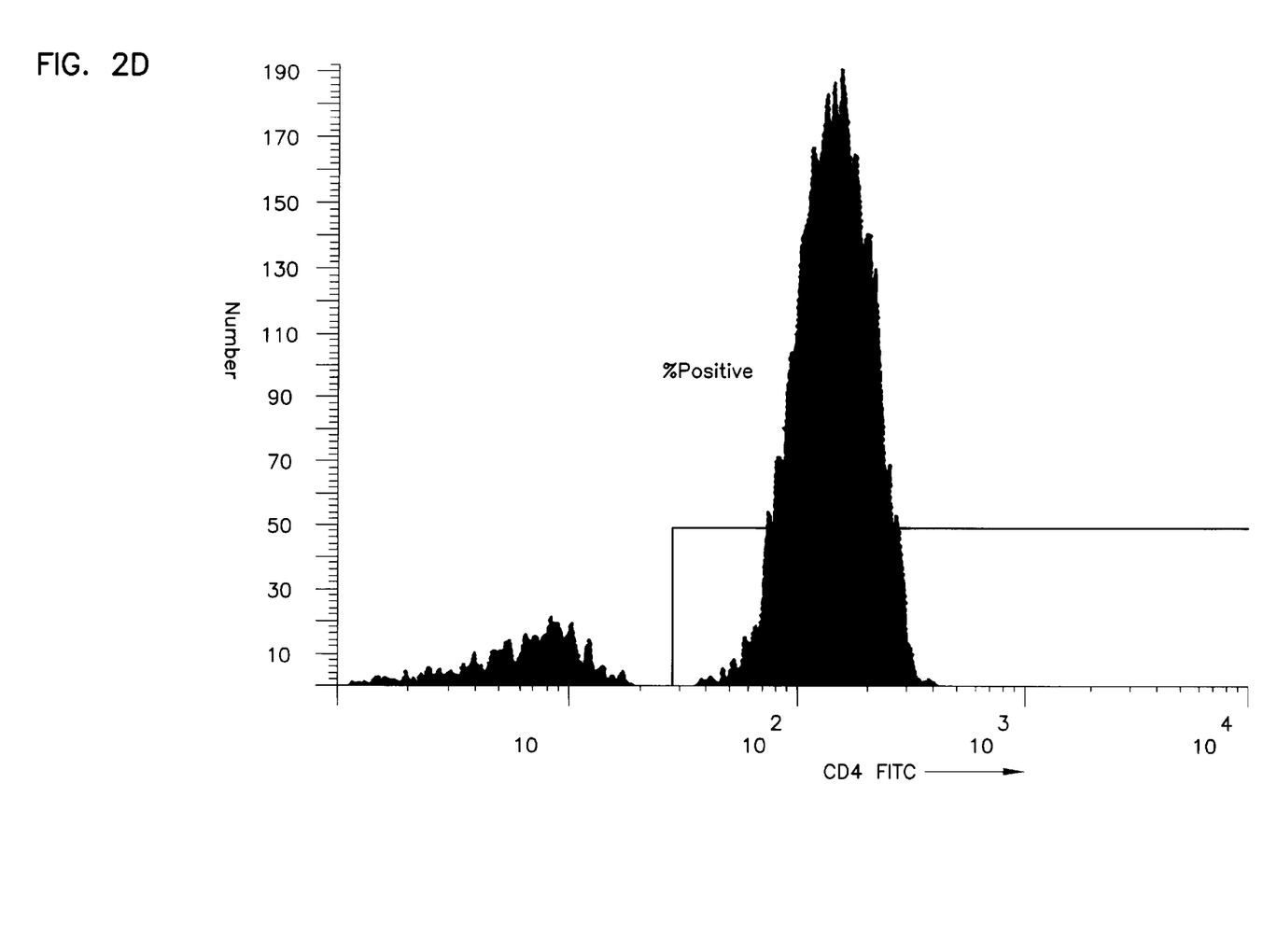

An improved positive selection system is developed (FIG. 1) in which a cell suspension containing a targeted cell population whose enrichment is sought is reacted with a first reagent recognizing a cell type. The first reagent is a monoclonal antibody or antibody fragment directed to surface antigens on the cell type. Unreacted first reagent is then removed by washing. The cell suspension containing the first reagent/cell type complexes is next reacted with a biotinylated second reagent. This has specificity for the first reagent and binds to it. Biotinylated second reagent/first reagent/cell type complexes are thus formed. Excess biotinylated second reagent is then removed by appropriate washing.

The term "biotin", as used herein, includes not only biotin itself, but also derivatives of biotin in which the binding between the derivative of biotin and its specific binding partner is substantially equivalent to that between biotin itself and the specific binding partner. These derivatives include iminobiotin and biotin covalently conjugated to a spacer, such as ε-caproamidobiotin. Other derivatives of biotin, such as those incorporating spacers of varying lengths, can also be used.

The term "avidin", as used herein, includes not only avidin itself, but also derivatives of avidin that are modified or coupled to another protein, and streptavidin.

The term "cell", as used herein, can include both prokaryotic cells and eukaryotic cells unless otherwise specified.

The first reagent and second reagent are typically antibodies or antibody fragments, such as Fab, F(ab'), F(ab')$_2$, or Fv fragments, but can be other molecules that specifically bind to a specific binding partner with an affinity that is comparable to the binding of an antibody to its corresponding antigen or hapten. The term "antibody," as used herein, also includes chemically modified intact antibody molecules and antibody fragments, including hybrid antibodies assembled by in vitro reassociation of subunits and single-chain antibody molecules produced by genetic engineering.

In some systems according to the present invention, a biotinylated first reagent may be used. This first reagent can be one that is either covalently linked to biotin or noncovalently linkable with biotin. This would obviate the need for a biotinylated second reagent.

Typically, the first reagent is a monoclonal antibody specific for a cell surface antigen and the second reagent is a biotinylated antibody specific for the first antibody.

In a preferred embodiment, the first reagent is a mouse monoclonal antibody while the second reagent is a biotin-labeled anti-mouse immunoglobulin.

The next step is providing a solid capture surface onto which an immobilized ligand is covalently linked, the ligand being a member of a ligand-antiligand pair and capable of existing in soluble form. Then, a biotinylated antiligand is noncovalently adsorbed to the solid capture surface. The next step is reacting the cell suspension containing the biotinylated second reagent/first reagent/cell type complexes with the solid capture surface to which the biotinylated antiligand is adsorbed and with avidin to bind the biotinylated second reagent/first reagent/cell type complexes to the biotinylated antiligand through an avidin bridge to bind the cell type to the solid capture surface. Typically, the biotinylated antiligand is first reacted with avidin and then the biotinylated antiligand/avidin complex is then bound to the solid capture surface by the reaction of the antiligand with the ligand. The reaction with the biotinylated second reagent/first reagent/cell type complexes then follows. Alternatively, the biotinylated antiligand can be adsorbed onto the solid capture surface first, and avidin and the biotinylated second reagent/first reagent/cell type complexes are then added to form the complete complex.

Typically, the solid capture surface is prepared by first covalently immobilizing heparin as an immobilized ligand, onto which a precisely controlled mixture of biotinylated antithrombin III/avidin complex is adsorbed. Antithrombin III is a plasma glycoprotein of 58 kd that specifically binds heparin. The binding of heparin to the solid capture surface is described below in Example 2, using an aldehyde-activated resin. Other methods for binding molecules such as heparin to solid phases are known and are described, for example, in G. T. Hermanson et al., "Immobilized Affinity Ligand Techniques" (Academic Press, San Diego, 1992). This reference describes the activation of heparin with cyanogen bromide and its immobilization on an agarose matrix.

In this typical alternative for the order of reaction, the cell suspension containing the biotinylated second reagent/first reagent/cell type complexes is next reacted with the solid capture surface containing the avidin-complexed antithrombin III molecules bound to heparin in order to bind the complex to the avidin bridge positioned between the heparinized surface bound antithrombin III molecules, thereby forming insolubilized heparin/biotin-antithrombin III/avidin/biotinylated second reagent/first reagent/cell complexes. This binds the cell type to the solid capture surface. As described above, other orders for the reactions are possible.

The next step is eluting the cell type from the solid capture surface by dissociating the ligand-antiligand binding pair with soluble ligand, thus producing eluted cells of the cell type. Typically, when the ligand-antiligand pair is heparin and antithrombin III, the cells are eluted by dissociating the heparin/antithrombin III complex with an elution medium containing soluble heparin. This provides an improved immunoselection technique for dissociating and recovering the eluted cells of the cell type from the capture surface.

Heparin and antithrombin III are members of a ligand-antiligand pair and allow affinity elution of the matrix-bound cells with excess heparin in a standard, packed-bed column chromatography format. The binding affinity of heparin-antithrombin III complexes is high ($K_d \approx 10^{-8}$ M) but this complex is far less stable than the avidin-biotin complex ($K_d \approx 10^{-15}$ M). Therefore, it is likely that in the presence of competing ligands, e.g. the clinical anticoagulant heparin or some blood plasma proteins, this linkage could be weakened or dissociated. We reasoned that the stability of heparin-antithrombin III complex might be increased by suitable crosslinking of antithrombin III. An appropriate crosslinker could be avidin if the antithrombin III molecules were biotinylated. Avidin, being a tetrameric protein having four biotin binding sites, could interpose between the antithrombin III molecules and form very stable bridges. This could greatly increase the overall binding strength of the heparin-antithrombin III complex. The other unoccupied biotin binding sites on the avidin molecule might still be available to bind the biotinylated second reagent/first reagent/cell complexes.

These assumptions turned out to be correct. First, the biotinylated antithrombin III/avidin complexes were found to bind to the immobilized heparin surface with a much higher affinity than biotinylated antithrombin III alone. Antithrombin III alone is completely dissociated from immobilized heparin resin at an ionic strength of 2M NaCl. However, the biotinylated antithrombin III/avidin complexes bound to the immobilized heparin surface much more strongly and even 4M NaCl, 4M $MgCl_2$ or 4M $CaCl_2$ cannot displace the complex.

Magnesium and calcium salts are strong chaotropes and are much more potent dissociating agents than NaCl. In this regard, the bound complex behaves much like the traditional immobilized avidin-biotinylated ligand interaction due to its tight binding to the heparin matrix. Thus we demonstrated that moderately strong surface-ligand interactions, such as those in which the dissociation constant of the ligand-antiligand complex is about $10^{-8}$ M, can be greatly increased in binding affinity by suitable crosslinking or polymerization of the adsorbed ligand. This improved linkage still remains susceptible to dissociation by a competing ligand, such as heparin. The dissociating heparin concentration is much higher than that used for clinical anticoagulation; therefore anticoagulated samples such as whole blood can be used in the separation without causing undesired early elution. The outlined concept should be applicable to other moderately strong surface ligand-antiligand interactions.

Methods according to the present invention can be employed for either positive or negative immunoselection. When the cell type is a target cell type whose isolation is desired, the method is a positive immunoselection method. Such target cell types can include, but are not limited to, hematopoietic stem cells, tumor cells, fetal cells from the peripheral blood of pregnant women, lymphocytes, and virus-infected cells. When the cell type is an undesired cell type whose removal from the cell suspension is desirable, the immunoselection method is a negative immunoselection method. In such a negative immunoselection method according to the present invention, the target cells are enriched by removing one or more of the undesired cell types. In this version of the method according to the present invention, the first reagent has specific binding affinity for a surface molecule of an undesired cell type in the heterogeneous suspension. The undesired, contaminating, cell types, after removal by elution, can then be discarded.

The heterogeneous cell suspension can be derived from a source selected from the group consisting of bone marrow, peripheral blood, and cord blood. Other sources of heterogeneous cell suspensions can, alternatively, be used.

The solid capture surface can be presented in various forms, including particles, tubing, fibers, or mesh, and can be housed in other flowthrough devices such as columns or extracorporeal cartridges.

The selected cells can serve many purposes both in research and medicine. Hematopoietic stem cells can be selectively isolated from bone marrow or cord blood for treating hematological disorders, cancer or other diseases by gene therapy. For example, while bound to the column, the stem cells can be exposed to viral or other vectors for gene transfer and subsequent selection of transfected cells. Other applications may involve isolation of immature populations of peripheral lymphocytes which can then be exposed to growth factors suitable for directing their maturation and expanding their population. Lymphokine activated killer cells (LAK) can be raised this way for autologous reinfusion into the patient for cancer therapy. Negative cell selection can be used to correct abnormalities in lymphocyte populations involving excessive numbers of circulating cells. Tumor cells or T cells can be removed from blood or bone marrow. Circulating viruses or parasites can also be removed from blood using the subject invention. The cell separation method can also be used as a sensitive diagnostic assay for detecting the presence of tumor cells in a patient's bloodstream or bone marrow. This allows the discovery of micrometastases and thus has a prognostic value in cancer therapy. The efficiency of monoclonal antibody production techniques can also be enhanced using the subject invention. For example, tumor cell specific lymphocytes can be specifically isolated and then fused with transformed cells to produce hybridomas. This obviates the need for the typical massive screening of fused cells. This should accelerate hybridoma development and allow customization of antibody production for single patients.

Although this method is described with particular application to the isolation of cells, it can also be used to isolate other biological entities that can be bound by the appropriate specific binding partners, such as subcellular structures and viral particles.

The following Examples illustrate the advantages of the subject invention. Accordingly, it is to be understood that the description in this disclosure is to facilitate comprehension of the invention and should not be construed to limit the scope thereof as persons skilled in the art can, in light of this disclosure, can generate additional embodiments without exceeding the scope or departing from the spirit of the claimed invention.

EXAMPLE 1

Biotinylation of Antithrombin III

Human plasma-derived, pure, clinical grade antithrombin III was biotinylated as follows. Antithrombin III (Alpha Therapeutic Corporation, Los Angeles, Calif.) was dialyzed in 50 mM sodium acetate, pH 5.5, and adjusted to a concentration of 2 mg/ml. Sodium metaperiodate (Sigma Chemical Co., St. Louis, Mo.) was added to a final concentration of 1 mM and the mixture was kept in the dark at 0° C. for 30 min. The mixture was dialyzed in the same acetate buffer at 4° C. overnight. Biotinhydrazide was then added to 10 mM final concentration and the mixture gently stirred for 2 h at room temperature. The mixture was dialyzed in phosphate-buffered saline (PBS; 8 mM $Na_2HPO_4$, 0.15 mM $KH_2PO_4$, 0.137M NaCl, 2.7 mM KCl, pH=7.4), filtered through a 0.2 $\mu$m filter and stored in aliquots at −20° C.

EXAMPLE 2

Heparin Conjugation to Solid Phase Adsorbent

Aldehyde activated ALD Cellthru Bigbead (Sterogene Bioseparations, Inc. Carlsbad, Calif.) was washed with 0.1M sodium phosphate at pH 7.0 ("coupling buffer"). Heparin sodium was dissolved in coupling buffer at a concentration of approximately 2 mg/ml and then continuously mixed with the gel for 1 hour at room temperature. ALD Coupling solution (Sterogene Bioseparations, Inc. Carlsbad, Calif.) was then added to 0.1M final concentration and the reaction allowed to proceed overnight. After washing, the gel was stored in PBS with 0.1% sodium azide at 4° C. The gel was resuspended in a 10 mM imidazole, 30 mM NaCl, pH 6.8 buffer ("binding buffer") just before adsorption of the antithrombin III-avidin complex.

EXAMPLE 3

Labeling of Lymphocytes

Concentrations of antibodies utilized in these experiments were based on immunofluorescence staining which demonstrated that a minimum of 2 $\mu$g of primary antibody for $10^7$ cells and 0.5 $\mu$g biotinylated second antibody per $10^7$ cells were respectively required to saturate the binding sites for CD4 on T cells (not shown). Buffy coat cells were obtained by Ficoll-Hypaque (specific gravity=1.077; Pharmacia) density gradient centrifugation from freshly drawn blood samples (10–50 ml) obtained from healthy donors. Ten million cells per ml of buffy coat cell mixture were incubated for 30 minutes with a CD4 antigen specific mouse monoclonal antibody in PBS with 2% BSA (PBS/BSA) at 4° C. Cells were washed twice after incubation with monoclonal antibody and twice again after incubation with the secondary antibody, biotinylated goat anti-mouse immunoglobulin G (b-GAMIg) for 30 minutes at 4° C.

EXAMPLE 4

Preparation and Use of Immobilized Heparin Column

The heparin-conjugated gel (3 ml) from Example 2 was packed into Kontes columns (4.5 ml total volume). The screens on the column end-pieces were replaced with 180 $\mu$m porosity nylon screens. Biotinylated antithrombin III (0.5 mg/ml resin) was added and the column gently agitated for 45 min. Unadsorbed protein was removed by washing with binding buffer. Avidin (1.5 mg/ml resin) was subsequently added to the biotin-antithrombin III-coated resin and then the resin was washed with PBS. Ten million antibody-treated cells were suspended in a solution of 0.5 ml PBS/BSA. The cell suspension was slowly passed through a 3 ml column bed of the heparin/biotinylated antithrombin III/avidin-adsorbed gel using PBS/BSA until a total of 10 ml of eluate was collected. By trypan blue dye exclusion, cell viability was found to be greater than 90%. To remove nonspecifically entrapped cells, the gel bed was washed with PBS/BSA and then the same buffer containing 50 mg/ml heparin was added to elute adherent cells.

The cells eluted in a sharp, concentrated peak. This indicated effective elution by the heparin ligand.

Several cell separation techniques have been developed utilizing immunoselection in different formats. The avidin-biotin immunoadsorption technique allows binding of cells to solid phases, but recovery of adherent cells has been difficult due to the very strong linkage between avidin and biotin. The primary elution method is mechanical shear which may damage cell membranes and affect cell viability and function. The relatively small particle size of the immobilized avidin adsorbents increase nonspecific cell entrapment. This technique is difficult to scale up from research systems to large scale cell separation. Other cell separation procedures have further disadvantages. The "panning" technique employs plastic tissue culture dishes coated with antibodies. This method is simple but the yield and purity of adherent cells is variable. Also, panning is cumbersome in large scale cell separation. The fluorescence activated cell sorter has a limited throughput which makes it impractical for large scale operation. This method incurs the largest operating costs. Both panning and the fluorescence activated cell sorter are open systems which require expensive clean room environment for scaleup. In contrast, immunoaffinity column chromatography is easy to scale and can be adapted to the separation of cells on the scale of several hundred million cells per run. Besides antibodies, other examples of such interactions include ligands such as protein A, fluorescein, plant lectins or goat antimouse immunoglobulin linked to solid phases. These affinity column procedures employ moderately strong binding interactions ($Kd \approx 10^{-7}$–$10^{-10}$ M) between antibody on the solid phase and cell surface antigen. As a result of this, cell retention on the adsorbent column may be incomplete even after longer incubation periods which may also promote nonspecific cell retention. The heparin/antithrombin III ligand-antiligand system of the subject invention is also classified as a moderately strong interaction. We have found that the stability of heparin-antithrombin III complex can be greatly increased by crosslinking antithrombin III with avidin following biotin labeling of the antithrombin III molecules. Avidin, being a tetrameric protein with four biotin binding sites, interposes between the antithrombin III molecules forming very stable bridges. This greatly increases the overall binding strength of the heparin-antithrombin III complex. The unoccupied biotin binding sites on the avidin molecule are available to bind the biotinylated second reagent/first reagent/cell complexes. In this regard, the heparin/biotinylated antithrombin III/avidin complex operates much like the immobilized avidin itself with the additional capability of rapid elution of isolated cells with the competing ligand heparin. Therefore, there is no need for mechanical shear or enzymic digestion to release the cells from the surface of the solid phase particles. An additional advantage is that it is possible to set up a closed system for large scale separations so clean room operation is not necessary. The outlined method can be applied to other moderately strong surface ligand-antiligand interactions.

ADVANTAGES OF THE INVENTION

The present invention provides an improved method for immunoselection of cell types. It can be used for both positive and negative selection. It can be scaled up readily while providing highly specific selection of cells. It can be used with many types of heterogeneous cell suspensions to isolate any type of cell for which an appropriate specific binding partner for a surface marker exists. The use of avidin as a bridge increases the stability of the ligand-antiligand interaction, thus reducing contamination of the eluted cells as a result of nonspecific dissociation. The method does not require harsh conditions, such as extremes of pH or mechanical shearing, and preserves the viability and biological properties of the eluted cells.

It will be understood that in giving the preferred embodiment and application of the invention, the concept and scope of the invention is not limited to the specific reagents and reactions but certain changes and modifications may be practical within the scope of the appended claims. Therefore it is intended that the protection be limited only by the definitions of the appended claims.

We claim:
1. An immunoselection method for isolating a cell type from a heterogeneous cell suspension by affinity elution, comprising the steps of:
(a) reacting the cell suspension with a first reagent having specific binding affinity for a cell surface marker of the cell type in the heterogeneous suspension to form first reagent/cell type complexes in cell suspension, the first reagent being an antibody or antibody fragment specific for the cell surface marker;
(b) reacting the first reagent-cell type complexes with a biotinylated second reagent having specific binding affinity for the first reagent to form biotinylated second reagent/first reagent/cell type complexes in the cell suspension;
(c) providing a solid capture surface onto which an immobilized ligand is covalently linked, the ligand being heparin;
(d) noncovalently adsorbing to the solid capture surface a biotinylated antiligand, the biotinylated antiligand being antithrombin III;
(e) adding avidin to the adsorbed ligand-biotinylated antiligand complex formed in step (d) and then adding the cell suspension containing the biotinylated second reagent/first reagent/cell type complexes to the solid capture surface to which the biotinylated antiligand is adsorbed and to avidin to bind the biotinylated second reagent/first reagent/cell type complexes to the biotinylated antiligand through an avidin bridge to bind the cell type to the solid capture surface; and
(f) eluting the cell type from the solid capture surface by dissociating the heparin-antithrombin III binding pair with soluble heparin, thus producing eluted cells of the cell type.

2. The method of claim 1 wherein the cell type is a target cell type and the immunoselection method is therefore a positive immunoselection method.

3. The method of claim 2 wherein the target cell type is a cell type selected from the group consisting of hematopoietic stem cells, tumor cells, fetal cells from the peripheral blood of pregnant women, lymphocytes, and virus-infected cells.

4. The method of claim 1 wherein the cell type is an undesired cell type and the immunoselection method is therefore a negative immunoselection method.

5. The method of claim 1 wherein the first reagent is a monoclonal antibody specific for a cell surface antigen.

6. The method of claim 5 wherein the second reagent is a biotinylated antibody specific for the first reagent.

7. The method of claim 1 wherein the heterogeneous cell suspension is derived from a source selected from the group consisting of bone marrow, peripheral blood, and cord blood.

8. The method of claim 1 wherein the dissociation constant of the ligand-antiligand complex is about $10^{-8}$ M.

9. An immunoselection method for isolating a cell type from a heterogeneous cell suspension by affinity elution, comprising the steps of:
(a) reacting the cell suspension with a first reagent covalently or noncovalently linked to biotin; and having specific binding affinity for a cell surface marker of the cell type in the heterogeneous suspension to form biotinylated first reagent/cell type complexes in the cell suspension, the first reagent being an antibody or antibody fragment specific for the cell surface marker;
(b) providing a solid capture surface onto which an immobilized ligand is covalently linked, the ligand being heparin;

(c) noncovalently adsorbing to the solid capture surface a biotinylated antiligand, the biotinylated antiligand being antithrombin III;

(d) adding avidin to the adsorbed ligand-biotinylated antiligand complex formed in step (c) and then adding the cell suspension containing the biotinylated first reagent/cell type complexes to the solid capture surface to which the biotinylated antiligand is adsorbed and to avidin to bind the biotinylated first reagent/cell type complexes to the biotinylated antiligand through an avidin bridge to bind the cell type to the solid capture surface; and (e) eluting the cell type from the solid capture surface by dissociating the heparin-antithrombin III binding pair with soluble heparin, thus producing eluted cells of the cell type.

10. The method of claim 9 wherein the cell type is a target cell type and the immunoselection method is therefore a positive immunoselection method.

11. The method of claim 10 wherein the target cell type is a cell type selected from the group consisting of hematopoietic stem cells, tumor cells, fetal cells from the peripheral blood of pregnant women, lymphocytes, and virus-infected cells.

12. The method of claim 9 wherein the cell type is an undesired cell type and the immunoselection method is therefore a negative immunoselection method.

13. The method of claim 9 wherein the first reagent is a monoclonal antibody specific for the cell surface marker.

14. The method of claim 9 wherein the dissociation constant of the ligand-antiligand complex is about $10^{-8}$ M.

15. The method of claim 9 wherein the heterogeneous cell suspension is derived from a source selected from the group consisting of bone marrow, peripheral blood, and cord blood.

* * * * *